United States Patent
Turner et al.

(10) Patent No.: US 7,890,573 B2
(45) Date of Patent: Feb. 15, 2011

(54) SERVER-CLIENT ARCHITECTURE IN MEDICAL IMAGING

(75) Inventors: David Turner, Edinburgh (GB); Pavlos Papageorgiou, Edinburgh (GB); Conrad Chin, Edinburgh (GB); Carter Yates, Edinburgh (GB); Tom Kimpe, Ghent (BE)

(73) Assignee: Toshiba Medical Visualization Systems Europe, Limited, Edinburgh (GB)

( * ) Notice: Subject to any disclaimer, the term of this patent is extended or adjusted under 35 U.S.C. 154(b) by 653 days.

(21) Appl. No.: 11/282,957

(22) Filed: Nov. 18, 2005

(65) Prior Publication Data

US 2007/0115282 A1    May 24, 2007

(51) Int. Cl.
G06F 15/16 (2006.01)
(52) U.S. Cl. .................................... 709/203
(58) Field of Classification Search ................ 345/424; 709/217, 245, 203, 205, 209
See application file for complete search history.

(56) References Cited

U.S. PATENT DOCUMENTS

| | | | | |
|---|---|---|---|---|
| 5,808,617 | A * | 9/1998 | Kenworthy et al. | 345/421 |
| 6,377,257 | B1 * | 4/2002 | Borrel et al. | 345/419 |
| 6,384,821 | B1 | 5/2002 | Borrel et al. | |
| 6,424,996 | B1 * | 7/2002 | Killcommons et al. | 709/206 |
| 6,553,141 | B1 * | 4/2003 | Huffman | 382/232 |
| 6,556,724 | B1 * | 4/2003 | Chang et al. | 382/299 |
| 6,621,918 | B1 * | 9/2003 | Hu et al. | 382/128 |
| 6,718,192 | B1 * | 4/2004 | Samara et al. | 600/407 |
| 7,006,696 | B2 * | 2/2006 | Huffman | 382/232 |
| 7,013,032 | B1 * | 3/2006 | Samara et al. | 382/128 |
| 7,206,804 | B1 * | 4/2007 | Deshpande et al. | 709/203 |
| 7,290,011 | B2 * | 10/2007 | Eldar et al. | 707/104.1 |
| 7,689,599 | B1 * | 3/2010 | Shah et al. | 714/19 |
| 2002/0184238 | A1 | 12/2002 | Chylla | |

(Continued)

OTHER PUBLICATIONS

Engel K et al Institute of Electrical and Electronics Engineers: "Combining local and remote visualization techniques for interactive volume rendering in medical applications", Proceedings Visualization 2000. VIS 2000. Salt Lake City, UT, Oct. 8-13, 2000, Annual IEEE Conference on Visualization, Los Alamitos, CA: IEEE Comp. Soc, US Oct. 8, 2000, pp. 449-452, 587, XP010524637.

(Continued)

*Primary Examiner*—Firmin Backer
*Assistant Examiner*—Ebrahim Golabbakhsh
(74) *Attorney, Agent, or Firm*—Renner, Otto, Boisselle & Sklar, LLP

(57) ABSTRACT

A method of processing medical imaging volume data in a computer network is described. The method comprises loading a medical imaging data set to be processed to a server computer, processing the data set on the server computer, e.g. by executing a software application, and generating corresponding server-generated results. The server-generated results, e.g. rendered images, may then be transmitted to a client computer for display to a user. This allows users to quickly view the results of the processing because they have not had to wait for the data set to be transferred to their local machine before locally processing the data. However, while this is happening, the data set itself is also transmitted, e.g. as a background operation, to the client computer. Thus eventually the client computer has access to a local copy of the data set and may start processing the data set itself, thus freeing up server resources.

19 Claims, 9 Drawing Sheets

U.S. PATENT DOCUMENTS

| | | | |
|---|---|---|---|
| 2002/0184325 A1* | 12/2002 | Killcommons et al. | 709/206 |
| 2003/0055896 A1* | 3/2003 | Hu et al. | 709/205 |
| 2003/0086595 A1 | 5/2003 | Hu et al. | |
| 2003/0161398 A1* | 8/2003 | Feder et al. | 375/240.03 |
| 2004/0005094 A1* | 1/2004 | Huffman | 382/232 |
| 2004/0034723 A1* | 2/2004 | Giroti | 710/8 |
| 2004/0073546 A1* | 4/2004 | Forster et al. | 707/4 |
| 2004/0205758 A1* | 10/2004 | Hikawa et al. | 718/102 |
| 2005/0021656 A1 | 1/2005 | Callegari | |
| 2005/0114380 A1* | 5/2005 | Eldar et al. | 707/102 |
| 2005/0257257 A1* | 11/2005 | O'Connor et al. | 726/11 |
| 2005/0262065 A1* | 11/2005 | Barth et al. | 707/3 |
| 2006/0050818 A1* | 3/2006 | Morgan et al. | 375/350 |
| 2006/0190999 A1* | 8/2006 | Chen et al. | 726/11 |
| 2007/0046966 A1* | 3/2007 | Mussack et al. | 358/1.13 |
| 2007/0078729 A1* | 4/2007 | Brown | 705/26 |
| 2007/0130165 A1* | 6/2007 | Sjoblom et al. | 707/10 |
| 2007/0165935 A1* | 7/2007 | Deshpande et al. | 382/132 |
| 2008/0043015 A1* | 2/2008 | Valdiserri et al. | 345/419 |
| 2008/0044097 A1* | 2/2008 | Krishnan et al. | 382/251 |
| 2008/0081998 A1* | 4/2008 | Pan et al. | 600/458 |
| 2008/0140722 A1* | 6/2008 | Jakobovits | 707/104.1 |
| 2008/0207322 A1* | 8/2008 | Mizrahi | 463/32 |
| 2008/0232658 A1* | 9/2008 | Sugaya et al. | 382/128 |

OTHER PUBLICATIONS

Poliakov et al: "Server-based Approach to Web Visualization of Integrated Three-dimensional Brain Imaging Data" Journal of the American Medical Informatics Association, Hanley and Belfus, Philadelphia, PA, US, vol. 12, No. 2, Mar. 2005, pp. 140-151, XP005638570.

Ebara Y et al: "Remote Visualization Using Resource Monitoring Technique for Volume Rendering of Large Datasets", Applications and the Internet, 2004. Proceedings. 2004 International Symposium on Tokyo, Japan Jan. 26-30, 2004, Los Alamitos, CA, USA, IEEE Comput. Soc, US, Jan. 26, 2004, pp. 309-312, XP010682169.

Krokos M et al: "Towards Fast Volume Visualisation on the WWW", Information Visualization, 1999. Proceedings. 1999 IEEE International Conference on London, UK Jul. 14-16, 1999, Los Alamitos, CA, USA, IEEE Comput. Soc, US, Jul. 14, 1999, pp. 286-291, XP010346008.

* cited by examiner

SERVER-CLIENT ARCHITECTURE IN MEDICAL IMAGING

BACKGROUND OF THE INVENTION

The invention relates to server-client architectures in medical imaging, and in particular to processing of medical image data in a network environment.

Computer networks allow peripheral devices, data and computing applications to be shared amongst a number of users. This allows centralized management of a computing environment, helps reduce unnecessary duplication of computer resources, and can aid collaboration between users. For example, in a hospital or similar environment, it is common for patient data, e.g. medical image data, to be stored in a central data store from where it may be retrieved and subsequently processed, analyzed, viewed etc. by users working at computer workstations at different locations in the hospital (or working remotely over an appropriate link). This approach avoids the need for data to be stored locally to each of the users who might require it. Accordingly, the overall storage requirement of the computing system is much reduced. Furthermore, because there is only a single active copy of the data (there may be back-up copies), the integrity of the data and access control are easier to manage. This can be especially important in medical imaging applications, for example, to help reduce the likelihood that a clinician looks at a tampered, incomplete or accidentally modified version of the patient's medical data, or that an unauthorized person gains access to at the patient's data.

There are a number of different ways in which computing resources (e.g. memory and processors) can be distributed among clients and servers in a computer network environment. One way (and the more traditional for medical imaging applications) is the so-called "thick" client architecture, and another way is the so called "thin" client architecture.

FIG. 1 schematically shows a thick-client computer network 2 used in a hospital for processing and viewing medical image data. The network 2 comprises a server computer ("server") 4 and a series of (in this case four) client computer workstations ("clients") 6a-d. The server 4 and clients 6a-d communicate via a network interconnection 8, in this case a conventional a local area network (LAN) interconnection is used.

The server 4 includes a data store 10 in which medical image data are stored. This may be the central data store of the hospital providing long-term storage for all data, or it may be a limited-time or limited-purpose data store for a specific department such as radiology. In either case, the data store makes data accessible to the network 2. The server 4 further includes a data loader (not shown) which is operable to retrieve data from the data store 10 and to supply it to the network interconnection 8 through a server network-interface.

The client workstations 6a-d are identical to each other and comprise a display 12a-d and a client computer 14a-d. Each client computer 14a-d includes a client (or "local") processor 16a-d and a client (or "local") short-term storage memory 18a-d. The client processors 16a-d have sufficient processing power to run the applications the network supports, and each client memory 18a-d is large enough to store the amount of patient data required by these applications. The client computers 14a-d further include processing capability to perform tasks such as driving the display, receiving and processing user inputs from attached input devices (e.g. keyboards and mouse pointers), and network communication.

FIG. 2 schematically shows a typical workflow in the thick-client network shown in FIG. 1. All four of the client workstations are active in processing medical image data. There are three main stages to the workflow which are relevant here.

Firstly, the server 4 sends patient data from its data store 10 to the local memories 18a-d of each client workstation 6a-d. This is shown schematically in FIG. 2 by arrows labeled W1, and also by shading of the client memories 18a-18d indicating that they contain patient data. The transfer of patient data is preferably done ahead of the time that the data is needed by a user of one of the client workstations 6a-d, for example during the previous night. Because the client memories 18a-d are smaller than the size of the server's data store, data to be transferred in advance are selected in accordance with certain rules. For example, data selected for ahead-of-time transfer to a given client workstation can be based on the clinical specialty of the user of the client workstation, the location of the client workstation in the hospital, recently accessed data for that workstation, or simply a random distribution of data from different patients, for example.

Secondly, when users at each of workstations 6a-d wish to work with data associated with a particular case, the relevant patient data is loaded from the associated local memory to the corresponding client processor 16a-d (which is running the imaging application being used by the user). This is schematically shown in FIG. 2 by the arrows labeled W2. The client processors 16a-d are shown shaded in FIG. 2 to indicate that they are processing data. If the required data are not already in the local memory 18a-d, they must be retrieved from the server's data store 10 over the network interconnection 8. This can take a significant amount of time due to the large size of typical medical imaging data sets.

Thirdly, images generated by the various client processors running the imaging application are displayed to the user on the displays. This step is schematically indicated in FIG. 2 by arrows labeled W3.

In brief summary, in a thick-client medical imaging network such as shown in FIGS. 1 and 2, the intensive computational tasks associated with generating images, e.g. image rendering, are performed locally on locally stored copies of data obtained from the server data store 10.

The main drawback of the thick-client approach is the reliance on transferring patient data ahead of time to each client workstation. This limits the flexibility of the user's workflow (e.g. by requiring them to indicate the day before what work they will be doing the following day), and cannot cope with emergencies, such as an emergency medical case. As noted above, it is possible to download a patient's data on demand from the server when a user requests to open a patient study that is not contained in the current locally stored data. However, this is undesirable because the patient data for any given study is large (from hundreds of megabytes up to a few gigabytes) and thus transmitting patient data on demand requires the user to wait up to several minutes for the data to arrive over the network.

FIG. 3 schematically shows a thin-client computer network 22 used in a hospital for processing and viewing medical image data. To some extent this may be considered to operate in an opposite manner to the thick-client network of FIGS. 1 and 2. The thin-client network 22 comprises a server computer ("server") 24 and a series of (again four) client computer workstations ("clients") 26a-d. The server 24 and clients 26a-d communicate via a network interconnection 28, again this is a conventional LAN.

The server 24 includes a data store 30 in which medical image data are stored. As with the network 2 shown in FIGS. 1 and 2, this may be the central data store of the hospital or a short term or departmental data store. The server 24 further includes processing capability which is shown schematically in FIG. 3 as four discrete processors 36a-d. The server processors 36a-d each have sufficient processing power to run the imaging applications the network supports. The server 24 further includes a data loader (not shown) operable to retrieve data from the memory 30 and a server network-interface (not shown) allowing results of an application executed by the server processors (typically a succession of two-dimensional (2D) image frames rendered from three-dimensional (3D) medical image data) to be supplied to the network interconnection 28.

The client workstations 26a-d are identical to each other and comprise a display 32a-d and a client computer 34a-d. Each client computer 34a-d includes sufficient processing power to provide for a client network-interface and a display driver which together allow the client computers to receive the results of applications executed by the server processors (e.g. rendered images) and display them. The client computers are further able to receive and process user inputs from attached input devices and forward corresponding instructions to the server processor 36a-d so that a user can interact with the software application running, Commonly the client workstations may lack either the processing power, specialist processing resources such as a Graphics Processing Unit (GPU), or the memory to run the imaging application the network supports. I he client workstations may be conventional low-spec "desktop" PCs, or dedicated "dumb" terminals, for example.

FIG. 4 schematically shows a typical workflow in the thin-client network 22 shown in FIG. 3. There are two main stages to the workflow relevant here.

Firstly, in response to a request from a user of one of the workstations 26a-d to study a particular patient's data using a particular software application, the software application is initialized in one the server processors 36a-d, and the relevant patient data is retrieved from the data store 30 and loaded to the server processor. This is shown schematically in FIG. 4 for all four client workstations by arrows labeled V1.

Secondly, for each client workstation, the server processors process the data as appropriate under control of the software application and generate corresponding results, e.g. rendered images. The server processors 36a-d are shown shaded in FIG. 4 to indicate that they are working on processing data. The results of the processing are supplied via the server network-interface across the network interconnection 28 to the client network-interface of the various client workstations as appropriate. The client workstations then displays the results of the processing to the users on their displays. This is schematically shown in FIG. 4 by the arrows labeled V2. The arrows V2 are shown connecting directly from the server processors to the displays to indicate that the client is not playing a significant (in terms of processing resources) role in processing the data.

Because the resulting images to be displayed will often be much smaller (in terms of bytes) than the patient data from which they are derived, the thin-client approach is less prone to delays associated with network traffic. The thin-client scheme can be implemented by establishing a communication between the server and the client using a remote display protocol such as X11 or VNC, for example, or by establishing a proprietary communication with a program running on the client computer.

The thin-client network may still be heavily loaded (e.g. because a relatively low bandwidth network interconnection is employed), but the loading will be relatively continuous. This situation is often easier to engineer compared to a network that is frequently under utilized but has high peak bandwidth requirements (e.g. associated with data transfer in a thick-client network). Furthermore, because the server is aware of the activity of all users, it can more effectively employ predictive loading techniques to retrieve patient data from the data store 30 before they are needed.

Thus in a thin-client medical imaging network, the intensive computational tasks associated with generating images, e.g. image rendering, are performed at the server, with only the resulting images being transferred across-the network interconnection for display to a user. A key advantage of this approach is that the data path from the data store 30 to the server processors 36a-d can be a dedicated fast connection so that the server processors can quickly initiate processing of patient data from the data store on demand. Once the processing is complete, the resulting images can be transferred quickly for display to the user due to their small size.

The two alternative client-server architectures discussed above (i.e. thick-and thin-clients) each have their advantages and disadvantages, which are largely complementary. In the thick-client architecture, if the rules for distributing data ahead of time are not adequately effective, the user has to wait an objectionable amount of time for patient data to be sent to the client when demanded. In the thin-client architecture, the system is able to access patient data quickly, but as the number of clients increases, the server begins to encounter scalability limitations (i.e. difficulty adding more client workstations to an existing network or implementing a new network with a large number of client) in respect of both processing power and network bandwidth (because the server is doing the work for all clients and the network is continually transferring results to the clients). Thus it is not possible to keep adding client workstations as demand increases without decreasing performance for each user. Furthermore, because in a thin-client network the data processing that happens in response to user's input occurs remotely from the client workstation, there can be significant latency in responding to user inputs. This makes the system appear to be slow and unresponsive and can be frustrating for users.

Thus when implementing a network, deciding between a thick-or a thin-client architecture involves a tradeoff between potentially long waiting times to open a study (thick-client) and problems with scalability and latency during use (thin-client).

An approach between the above described extremes of "pure" thick-client and "pure" thin-client network architectures for image rendering is proposed in U.S. Pat. No. 6,384, 821 [1] and U.S. Pat. No. 6,377,257 [2]. These propose a scheme in which rendering tasks are split between a server and a client. The proposed scheme is for rendering synthetic data comprising a plurality of 3D geometric models representing different image objects to be rendered, with some objects (e.g. foreground objects) being rendered at the client in accordance with the thick-client approach and other objects (e.g. background objects) being rendered in lesser quality at the server, in accordance with the thin client approach. A composite of the separate renderings is then displayed to the user. However, this approach is primarily applicable to rendering synthetic images represented by a plurality of different geometric models which may each be rendered independently, such as when rendering a computer animated scene for a motion picture, computer game, or flight simulator. The approach is not practically applicable to rendering medical image data because medical imaging data typically comprise a continuous array of voxels representing a patient's body, or part thereof, that does not present any obviously advantageous decompositions between parts that can be rendered on the server and parts that can be rendered on the client. It is possible to separately render arbitrarily selected parts of the data on the client and parts on the server (possibly at different resolutions), but this is simply an example of parallel decomposition of the rendering task, and at best achieves a compromise between the goals of thin-client and thick-client configurations.

SUMMARY OF THE INVENTION

According to a first aspect of the invention, there is provided a method of processing medical imaging volume data in a computer network comprising: providing a volume data set to a server computer; initiating transfer of the volume data set to a client computer over the network; processing the volume data set at the server computer, by volume rendering or other medical image processing method for example, to generate image data and transmitting the rendered images, or other image data, over the network to the client computer for display during the transfer of the volume data set to the client computer; and switching to process the volume data set at the client computer after the transfer of the volume data set to the client computer is complete.

Because the data set is initially processed by the server computer, the server-generated rendered images quickly become available for display to a user. This is because it will generally be faster for the server computer to process the data set and transmit the resulting images to the client, than for the data set to be transferred to the client computer for local processing and generation of images for display. However, because the medical imaging data set itself is also transferred to the client computer, the client is able to operate independently of the server once the data set has been transferred. However, unlike in the traditional thick-client approach, this kind of autonomous operation by the client computer is achieved with the user still able to view the results of processing of the data set during the time in which it is being transferred to his location.

By in effect switching from a thin-client mode of operation to a thick client mode of operation in this way, the method can provide the advantages of both schemes. For example, as noted above the user is first able to rapidly view results of the processing by relying on the server's computational resources (an advantage of thin-client servicing). The user is then able to switch to working independently of the server so reducing the latency he experiences, and freeing up the computational resources of the server for other tasks such as serving other clients and also reducing network traffic (advantages of thick-client servicing).

Because the processing on the server computer may cease following transmission of the data set to the client computer, the scheme helps to overcome the problems of scalability which are associated with thin-client networks since network traffic no longer scales with the number of users running rendering processes.

When the data set has been transferred to the client, the method may include transmitting processing state data representing the operational state of the processing of the server computer from the server computer to the client computer, and configuring the client computer to a corresponding operational state so that it can seamlessly take over processing of the data set from the server computer.

The method may also comprise transmitting processing state data representing the operational state of the processing of the client computer from the client computer to the server computer. This can allow the server to monitor the performance of the client computer when it has taken over processing of the data, and, for example, retake control of the processing is it becomes apparent that the server computer could perform the processing more efficiently, perhaps because it presently has a significant excess of spare processing capacity, or because the client computer is beginning to reach its limitations.

The method may include the data set being transmitted to the client computer from the server computer, e.g. as managed by the server computer, or in the case that the client has direct access to the source of the data (data store), the client may retrieve the data set directly from there.

The data set may be transferred to the client during periods of inactivity on the network, for example at times when there is no requirement for the server-generated rendered images to be transmitted to the client. This might be the case because the user spends some time looking at a static image, for example. If new rendered images are subsequently required before all of the data set has been transferred, the transfer of the data set may cease until the next period of network inactivity to allow optimum performance of the network in supplying server-generated rendered images.

Alternatively, the data set may be transmitted to the client computer in parallel with the server-generated rendered images, e.g. using a fixed fraction of the bandwidth. Thus a trade off between optimum serving of server-generated rendered images and reducing the time before the client can start to operate autonomously may be made.

To further improve performance, the rendered images and the data set may be compressed before transmission. This may be a lossy or a lossless compression, depending on the quality requirements of the user. Improved overall transfer rates may also be achieved if different aspects of the transfer (e.g. different components of the server generate results) are compressed using different algorithms.

Furthermore, the data set may be compressed so that it can be transferred quickly to the client computer and allow it to operate in an autonomous mode earlier than could if an uncompressed data set were transferred, but then an uncompressed (or less compressed) data set may be transferred so the client can operate in an autonomous manner using the higher quality data set when it has received it. Processing may occur in parallel on both the client (on the initially transferred compressed data) and on the server and rendered results from either used according to context (e.g. from server for static images and from client for moving images).

The method may further comprise waiting for a period of time before initiating transfer of the volume data set to a client computer over the network. This can ensure data are not transferred if a user is only viewing a patient's data for a short period.

According to a second aspect of the invention, there is provided a computer network configured to perform the method of the first aspect of the invention.

According to a third aspect of the invention there is provided a computer program product of a volume rendering application for displaying rendered images of volume data sets to a user, wherein the application is operable on a network interconnecting a server computer and a client computer to: access a volume data set on the server computer; initiate transfer of the volume data set to a client computer over the network; perform volume rendering by processing the volume data set at the server computer and transmitting the rendered images over the network to the client computer for display during the transfer of the volume data set to the client computer; and switch to process the volume data set at the client computer after the transfer of the volume data set to the client computer is complete.

BRIEF DESCRIPTION OF THE DRAWINGS

For a better understanding of the invention and to show how the same may be carried into effect reference is now made by way of example to the accompanying drawings in which.

DETAILED DESCRIPTION

Figure 5:
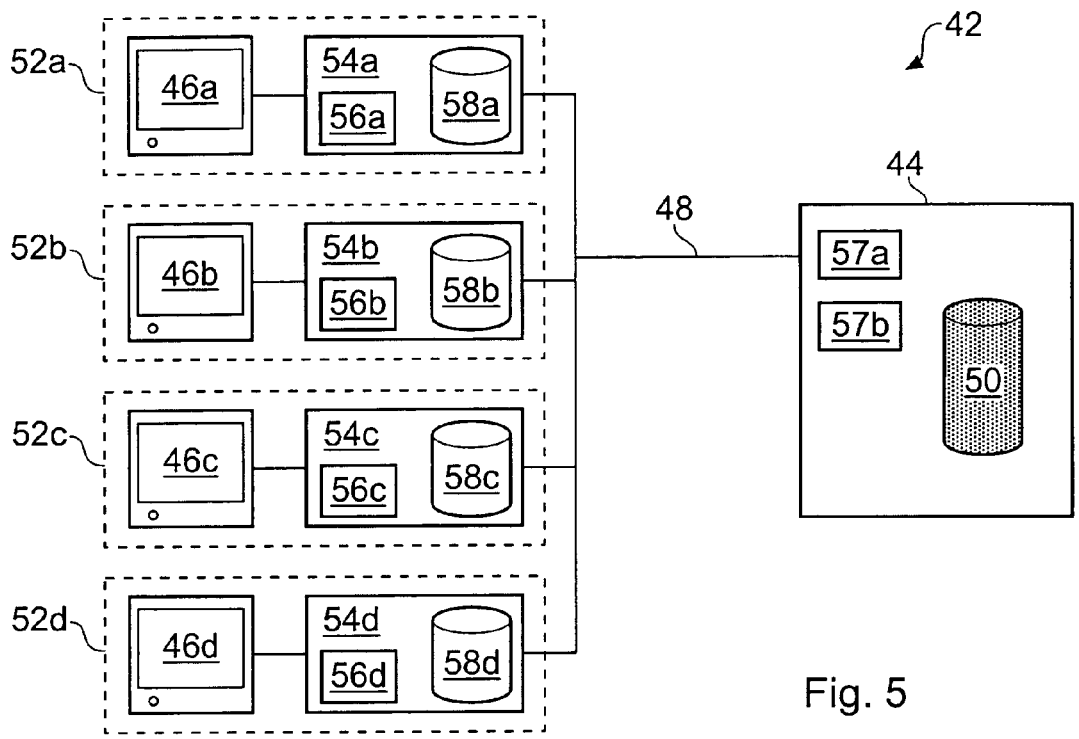
FIG. 5 schematically shows a computer network used in a hospital for processing and viewing medical image data according to an embodiment of the invention.

FIG. 5 schematically shows a computer network 42 for analyzing (e.g. processing and viewing) medical image volume data according to an embodiment of the invention. The data are analyzed using a software application. A typical software application supported by the network will comprise a suite of programs which allow a user to view and manipulate patient data as required for a given clinical study. An example of this type of application is Voxar3D™ provided by Barco N.V. A common task will be to render 2D images from 3D medical imaging data. The network 42 is deployed in a hospital, or similar environment. However, it could also be a distributed network (e.g. using the internet) that is not linked to any particular physical location. The network 42 comprises a server 44 and a number of (in this case four) client computer workstations ("clients") 52a-d. The server 44 and clients 52a-d are in data communication through a conventional LAN network interconnection 48.

The server 44 includes a data store 50 in which medical image data may be stored for later retrieval. The data store 50 may be of the kind conventionally used in medical image data networks, such as in Patient Archival and Communication Systems (PACS) networks. Thus, the data store may comprise a hierarchy of storage levels ranging from fast-access relatively short-term storage to slower-access long-term storage. The arrangement and management of data in the data store may be in accordance with known schemes. The server 44 further includes processing capability to perform the conventional tasks of a server, e.g. data loading from the data store, interfacing with the rest of the network, and so on.

The server 44 further includes two server processors 57a, 57b. Each server processor (server computer) has sufficient processing power to run the software application(s) the network supports. It will be appreciated that the processing power of the server 44 is represented as two discrete processors only to aid explanation. In practice, the processing power provided by the two server processors shown in FIG. 5 may be provided by a single processor operable to run two processing threads, or by an array of more than two processing units working together. Furthermore, the choice of two server processors is also only for explanation. In practice the number of server processors (i.e. the number of separate processing threads the server can support) will depend on the size and utilization of the network. The number of server processors in a practical system will likely he more than two, although embodiments of the invention can include only a single server processor.

In this example, the client workstations 52a-d are identical to each other and comprise a display 46a-d and a client computer 54a-d. Each client computer 54a-d includes a client (or "local") processor 56a-d and a client (or "local") memory 58a-d. As with the server processors 57a, 57b, the client processors 56a-d have sufficient processing power to execute the applications the network supports. Furthermore, each client memory 58a-d is large enough to store the amount of patient data typically required by an instance of these software applications. The client computers 54a-d further include processing capability to perform tasks conventionally associated with client computers, such as driving the display, receiving and processing user inputs from attached input devices (e.g. keyboards and mouse pointers), network communication, and so on.

Figure 1:
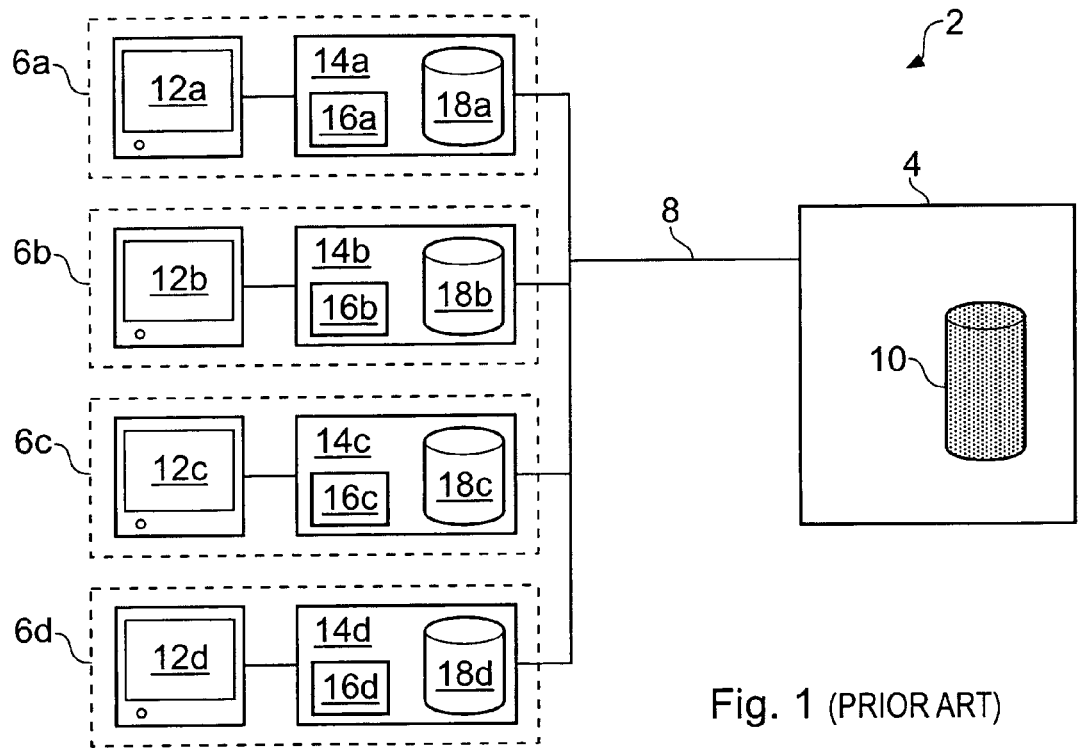
FIG. 1 schematically shows a thick-client computer network used in a hospital for processing and viewing medical image data according to the prior art.
Figure 2:
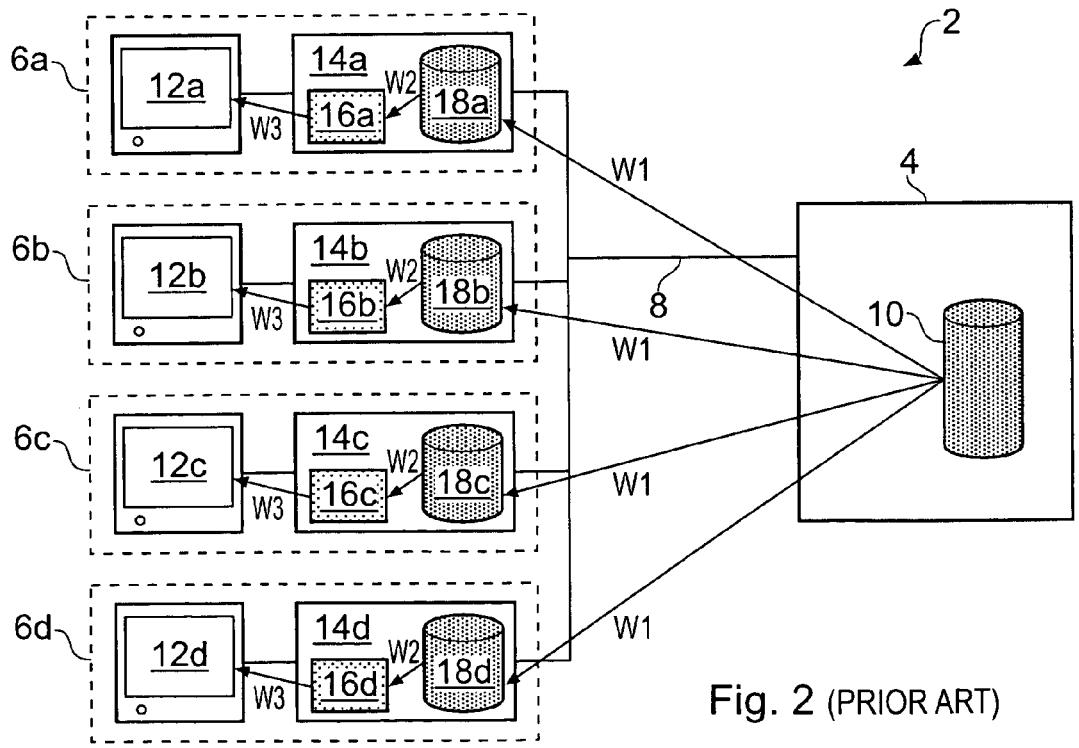
FIG. 2 schematically shows workflow associated with the thick-client computer network of FIG. 1.
Figure 3:
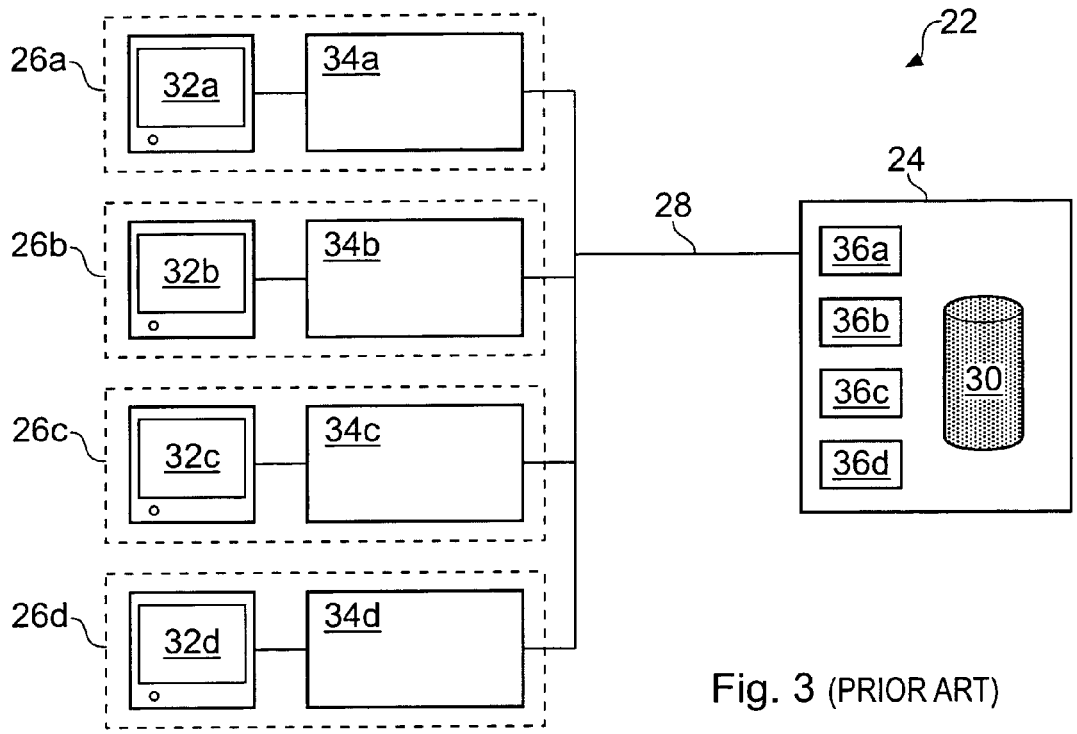
FIG. 3 schematically shows a thin-client computer network used in a hospital for processing and viewing medical image data according to the prior art.
Figure 4:
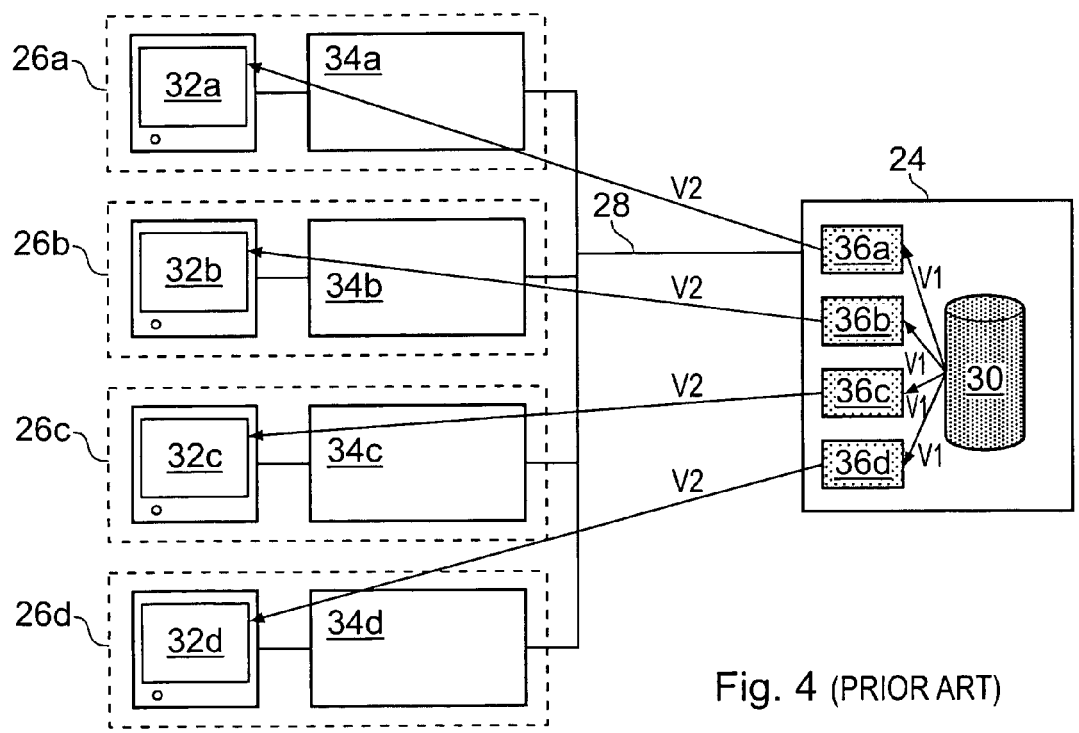
FIG. 4 schematically shows workflow associated with the thin-client computer network of FIG. 3.

Thus the network 42 shown in FIG. 5 differs from the "pure" thick-and "pure" thin-networks shown in FIGS. 1 and 3 respectively in that both the server and the client workstations include processors of sufficient processing power to execute the software application(s) used to analyze the medical imaging volume data.

Figure 6:
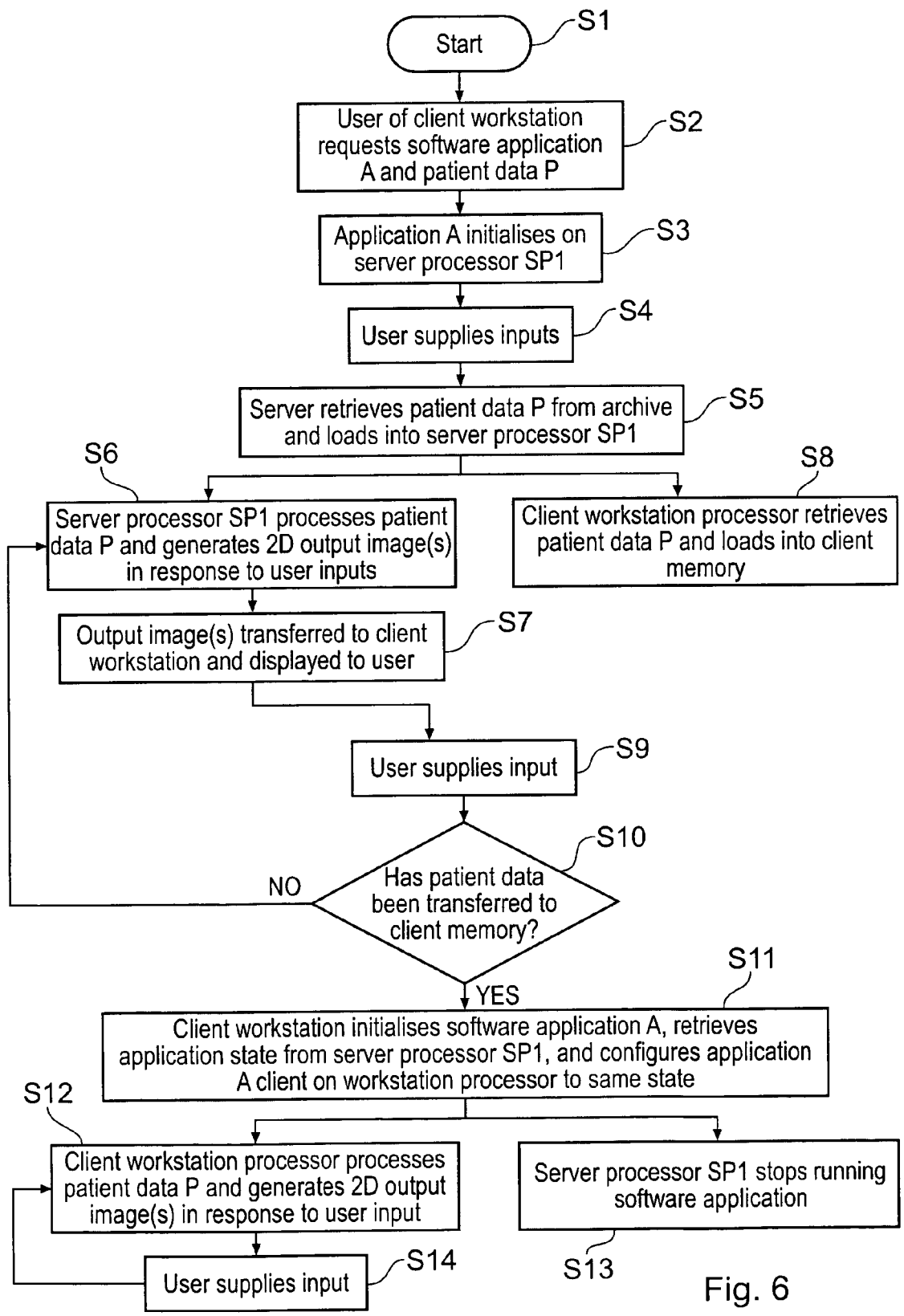
FIG. 6 is a flow chart schematically showing how the network shown in FIG. 5 may be used to run a software application for analyzing medical imaging data according to an embodiment of the invention.

FIG. 6 is a flow chart schematically showing a method of how the network 42 shown in FIG. 5 can be used to run an application for analyzing medical imaging data according to an embodiment of the invention. For simplicity, FIG. 6 shows the steps associated with a single user. However, in general there will be more than one user at any given time, and furthermore the users may start working at the different workstations at different times. The operation of the network with regard to multiple users is described in connection with each of steps shown in FIG. 6 below as appropriate.

In Step S1, the method starts. This step may correspond, for example, to a user "logging on" to one of the workstations. The method shown in FIG. 6 is the same regardless of which of the identical client workstations 52a-d is occupied by the user.

In Step S2, the user selects a software application to run and a patient's data to study (i.e. a data set for analysis). In this example it is assumed that the network supports multiple software applications and the user selects application A, and wishes to study patient data P. Software application A, might be a diagnostic radiology software application, for example. In some implementations, only one software application might be supported, or the client workstation may be tied to a specific software application, e.g. because it is in the radiology department, it may default to the main radiology software application supported by the network. Thus the user would not need to select an application. The patient data P is conventional medical imaging data, for example as obtained by a Computed Tomography (CT) scanner, Magnetic Resonance Imaging (MRI) scanner, or any other medical imaging modality. Furthermore, the data is collated in conventional form, for example it may accord to the Digital Imaging and Communications in Medicine (DICOM) format.

In Step S3, the software application A initializes (is made ready to execute) on one of the server processors 57a-b. It does not matter which of the server processors is selected to execute the application in any given instance (so long as the server processor is free, i.e. not already busy). For example, server processor 57a may be the default choice, but if that is already busy, then server 57b will be chosen. Here the selected server processor is referred to as SP1.

In Step S4, the user supplies inputs through the client workstation at which they are working to indicate how they would like the data to be analyzed. For example, the user input may stipulate that they wish to view a sagittal section view of a patient's CT scan with bone represented as shades of gray, blood vessels as shades of red, and all other body-tissue transparent.

In Step S5, the server retrieves patient data P from the data store 50 and loads it into server processor SP1 using conventional techniques.

In Step S6, the server processor SP1 executes the selected software application A to generate output results in accordance with the user wishes, e.g. by rendering the 3D patient data P using the render engine of the software application A to generate 2D) output images.

In Step S7, the server 44 supplies the resulting images to the client computer of the workstation used by the user via the network interconnection 48 and the client computer subsequently displays the image to the user on the associated display. Any measurements and other output information associated with the execution of the software application that may be relevant may also be transferred to the client workstation for display to the user. The transfer and display of the images (and any other relevant data) may be achieved using conventional techniques.

In performing Steps S1 to S7, the network 42 shown in FIG. 5 behaves as a thin-client network with the attendant benefit that the user is able to view output images without any significant delay associated with the need to transfer large amounts of patient data from the server to the client workstation.

Figure 7:
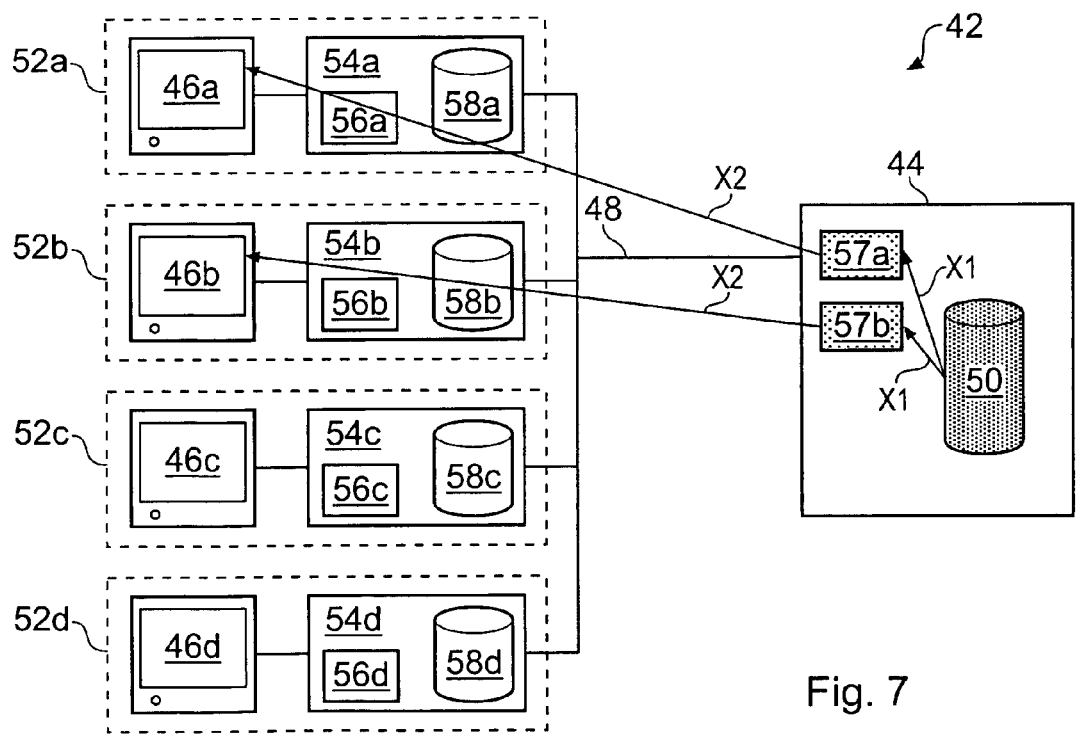
FIGS. 7 to 13 schematically show examples of workflow associated with the computer network of FIG. 5.

FIG. 7 shows the network 42 with the workflows associated with Steps S5 to S7 of the method shown in FIG. 6 schematically indicated. In FIG. 7 it is assumed that two of the client workstations (workstations 52a and 52b) are being used, while the other two workstations (workstations 52c and 52d) are not being used. This means Steps SI to S7 are being performed in two separate threads running in parallel. Thus one thread (here associated with client workstation 52a) employs server processor 57a, while the other thread (associated with workstation 52b) employs server processor 57b. Step S5 (loading data) is indicated for each thread by the arrows labeled X1. Step S6 (server processors executing software application) is indicated by both server processors 57a-b being shaded to indicate that they are working. Step S7 (transferring images to client) is indicated by arrows labeled X2. The arrows X2 are shown connecting directly from the server processors 57a-b to the displays 46a-b to indicate that the client processors 46a-b are not playing a significant (in terms of processing power) role in processing the medical image data. None of the client processors 56a-d are shaded and this indicates that they all idle, at least insofar as executing the software application is concerned. The client computers will, however, be performing the lightweight tasks associated with fetching display data from the network and sending it to the displays, collecting and processing user input, and, as described in further below, obtaining a copy of the patient data P.

In Step S8, which runs in parallel with Step S6, the client retrieves the patient data P being analyzed by the server processor SP1 across the network interconnection and loads it into its local memory. If the client is able to access the data store, it may retrieve the data directly from there. Otherwise, a part of the server's processing capability may be set aside for providing a copy of the patient data from the "working copy" in the server processor.

Thus while the server processor is executing the software application and serving images to the active client workstations, the same patient data P as is being analyzed is transmitted to the relevant client workstations. The transmission need not be time-critical and can be done using spare bandwidth, for example when the user is momentarily idle and there is no traffic between the server processors and the client workstation. Having the transmission of patient data occur in this way has the benefit of not affecting the way in which the network operates while it acts in a manner similar to a thin-client network. However, in the alternative, a fraction of network bandwidth may be set aside for transferring the patient data so that the data can be transferred quickly at the expense of less than optimal performance for the user viewing images as they are generated by the server. Beneficially, the network interconnection 48 may include sufficient bandwidth to allow transmission of images generated by the server at a rate deemed sufficient for typical applications (e.g. 30 frames per second) while having spare capacity for transmission of patient data from server to client.

Figure 8:
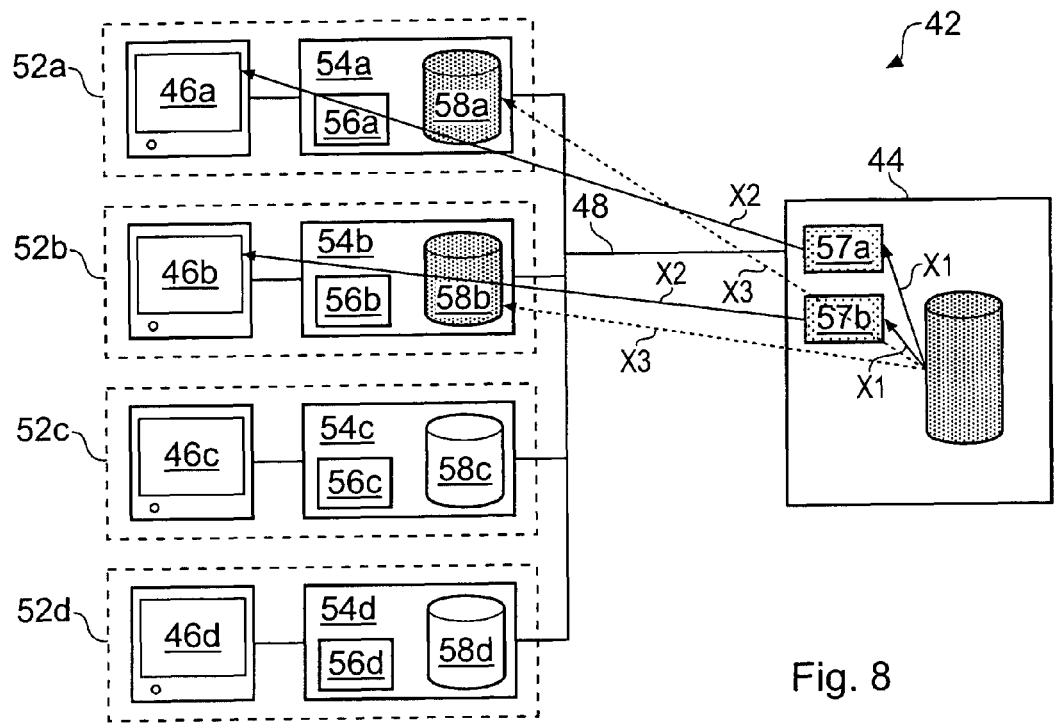

FIG. 8 is similar to FIG. 7, but additionally has the workflow associated with Step S8 of the method shown in FIG. 6 schematically indicated by dashed arrows labeled X3. These arrows represent the transfer of patient data P from the data store 50 (possibly via the server processors) to the client memories 58a-b associated with the client workstations currently in use. These client memories 58a-b are shown shaded to indicate that they now contain data.

In Step S9 of FIG. 6, the user supplies inputs through the client workstation at which they are working to indicate how they would like to proceed. For example, the user input may wish to generate another image corresponding to a rotation of the image currently displayed.

In Step S10, the client computer (or server, depending on which is governing this aspect of the operation) determines whether or not the patient data P has been transferred to the memory of the client computer. If not, the method follows the "NO" branch and returns to Step S6 in which the server processor SP1 continues to execute the software application and process the patient data in accordance with the user's wishes (i.e. by re-rendering the data to obtain a rotated image in response to the user input supplied in Step S9). Execution proceeds through Steps S7, S9 and S10 as above. During this time, Step S8 continues to execute in parallel.

Once it is determined in Step S10 that the patient data P has been transferred to the memory of the client computer, the method follows the "YES" branch to Step S11.

In Step S11, the software application A is initialized on the client processor associated with the client computer at which the user is working, and the client retrieves application state data (processing state data or metadata) from the server processor SP1 representing the operational state of the application at that time. The application state data is then used to configure the software application A on the client processor into the same state.

In Step S12, the software application A executes on the client processor such that the client processor begins to processes the patient data now stored in its local memory, generate images in accordance with the user's input, and display them to the user.

In Step S13, which runs in parallel with Step S11, the version of the software application A being executed on the server processor may stop as it is no longer needed. Thus server processor SP1 is freed up.

In Step S14, the user again supplies inputs through the client workstation at which they are working to indicate how they would like to proceed. The method then returns to S12 where the client processor continues to process the patient data and generate images for display to the user in accordance with the user's input. The method continues to repeat Steps S12 and S14 in sequence until the user finishes analyzing the data.

Figure 9:
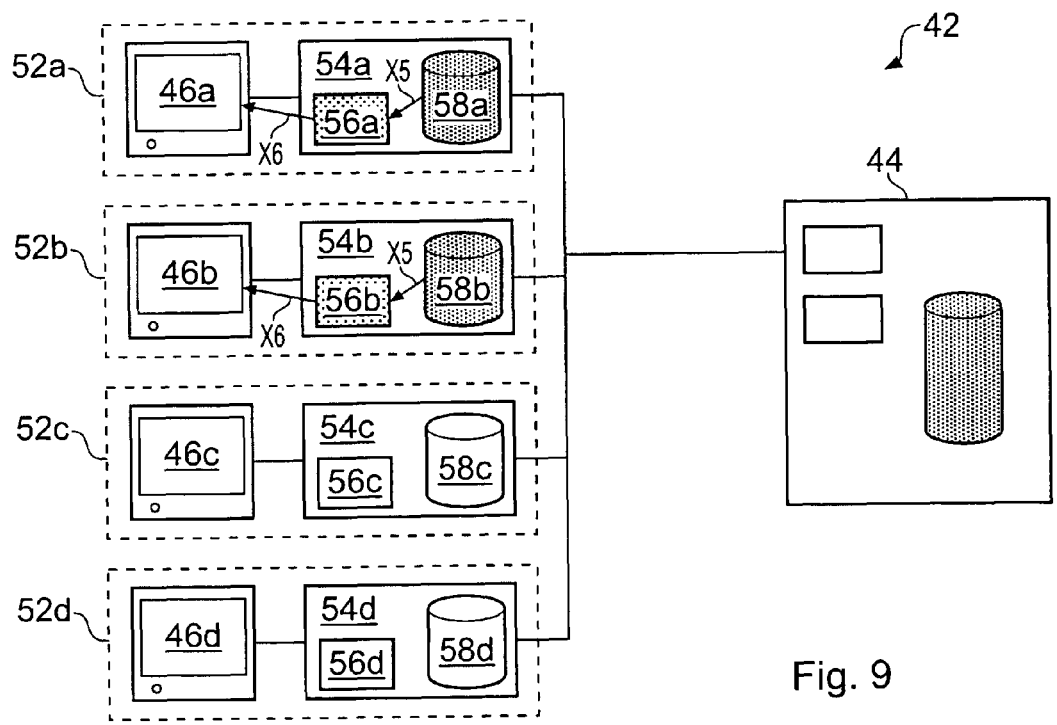

FIG. 9 is similar to FIGS. 7 and 8, but schematically shows the workflow associated with Steps S12 and S14. The client memories associated with the client workstations which are being used (client workstation 52a-b) are shown as shaded to indicate that they include patient data and the client processors associated with these client workstations are also shown as shaded to indicate that the processors are executing the software application. The loading of data from the local memories of the clients to the client processors is indicated by arrows labeled X5, and the displaying of images generated by the client processors on their associated displays is indicated by the arrows labeled X6. The server processors 57a-b are no longer shaded to indicate that they are no longer processing data.

Thus in repeating Steps S12 and S14, the network 42 effectively behaves as a thick-client network with the attendant benefits. Namely, there is reduced latency in responding to user requests, and because at this stage (i.e. when the patient data has been transferred to the client workstation) the execution of the software application associated with the client workstation does not require the server processor or network bandwidth, these resources are freed up and become available for other tasks (e.g. serving other client workstations in a thin-client like manner). This means the network does not suffer from the problems of scalability associated with "pure" thin network architectures. Thus in effect the network is able to switch transparently from a thin-client mode of operation to a more traditional thick-client mode of operation during use. The former achieves quick access to any given study and the latter achieves higher scalability of the overall system (by placing lower demands on the server).

The method continues to repeat Steps S12 and S14 in sequence until the user has finished studying the current patient data with the current software application. During this time, application state data (metadata) may be periodically transferred back from the client to the server so that the server can monitor the progress of the client. For example, if the server notes from this that one of the client workstations is struggling to keep up with the processing required of it, and if the server processor has current spare processing capacity, it may re-instigate execution of the application of the server and return to servicing the struggling client in a thin-client like manner as described above. Similarly, whether or not the server monitors the client's performance, the user may be provided with the option to return to a thin-client like mode of operation if he wishes, e.g. because he considers the client he is working at is not able to adequately meet his computing requirements. A further reason to transmit application state data (metadata) back to the server is to allow the server to effect recovery of the user's session (either using a server processor or a client processor) if the user's session is abruptly ended. For example, the user's session may end abruptly duo to a technical fault or because the user has to abandon their workstation to perform an emergency medical procedure. Recovery of user sessions in this way is a benefit typically associated with a thin-client mode of operation. When the user has completed his current analysis, he may finish at the client workstation altogether and "log off". If he does this, the patient data already transferred to the client workstation may (optionally, subject to a data security policy) remain in its memory since they may be a relatively high chance that the user will want to return to review the same data later. Thus if the user (or another user) does return to look at the same data, the software application call start executing on the client processor immediately without requiring support from the server. Alternatively, the user might not finish at the workstation completely, but may simply want to move on to study another patient's data, or to study the same patient's data using a different software application. If the user wants to look at another patient's data, the method returns to Step S2 (though the user may not be required to re-specify that he wants to run software application A). If, on the other hand, the user wants to use a different application to study the same patient data, the method may return to Step S11 (though with the new application being initialized on the client processor and thus with no application state data to be obtained from the server processor).

It will be understood that it is not necessary for all of the steps shown in FIG. 6 to be performed in the order shown. For example, some software applications may provide an interface by which a user selects a particular patient's data to study once the application is running. Thus the selection of patient data shown in Step S2 of FIG. 6 would be deferred until after the software application has initialized, e.g. after Step S3.

It will also be appreciated that it may not be necessary for all patient data to be transferred to the client computer before the client processor takes over execution of the software application. For example, it may be determined that enough data has already been transferred to allow the client processor to satisfy the user's immediate requirements based on the most recent user input. However, in terms of ease of implementation, it may be preferable to require all data that is likely to be needed to be transferred to the client before switching from a thin-client model to a thick-client model.

Throughout the above description, two of the client workstations (workstations 52c-d) have remained idle, as indicated by a lack of shading of their memories 58c-d and processors 56c-d in FIGS. 7 to 9. To demonstrate the improved scalability of the network 42 over a "pure" thin network, the operation of the network 42 when users log on to the two currently idle client workstations 52c-d of the system (while the first two users remain connected and active) is now considered.

As each new user logs on to one of as-yet unused client workstations 52c-d, the method shown in FIG. 6 executes as described above for each of the new users. Because the two client workstations 52a-b already in use are operating autonomously (thick-client mode) the two server processors 57a-d are free to service the new users in the manner described above.

Figure 10:
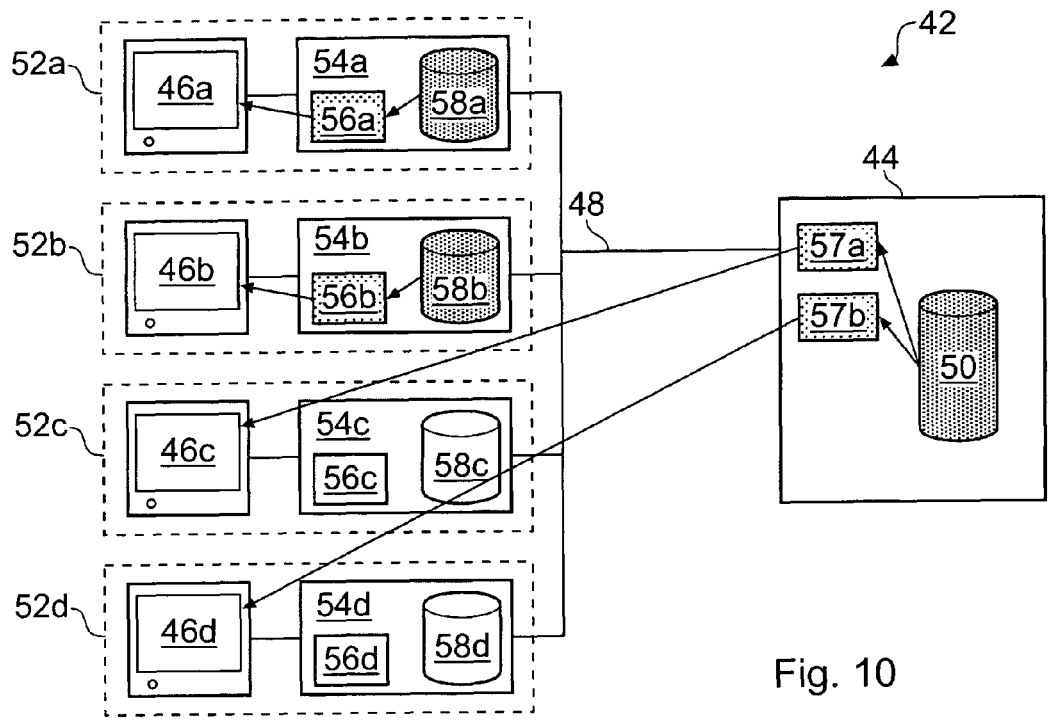
Figure 11:
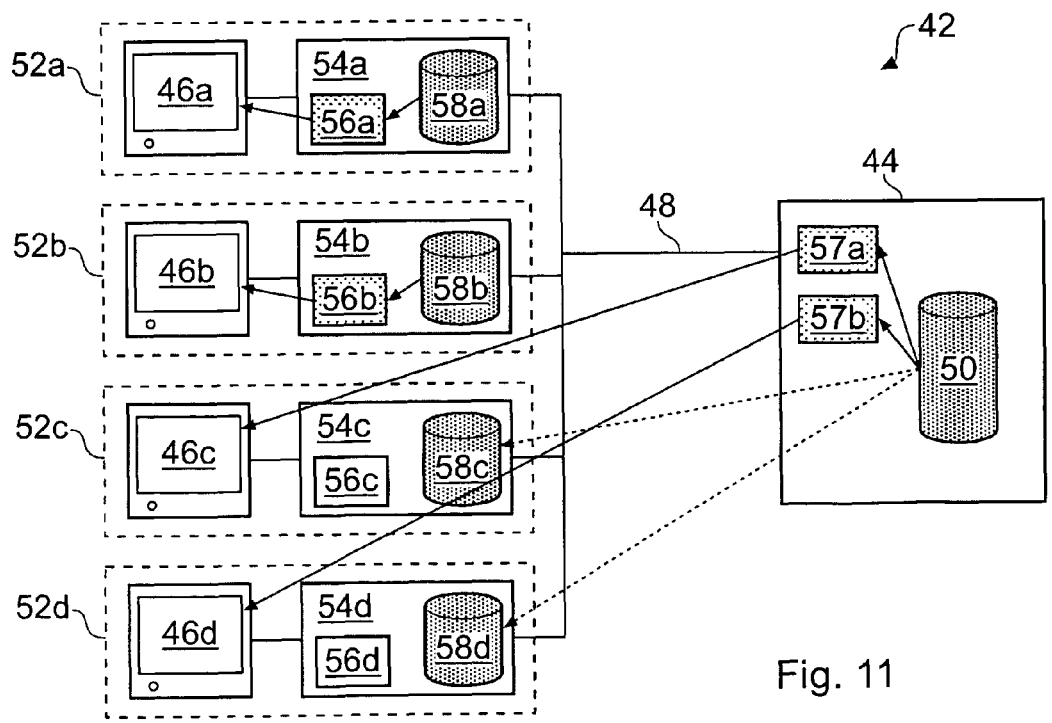
Figure 12:
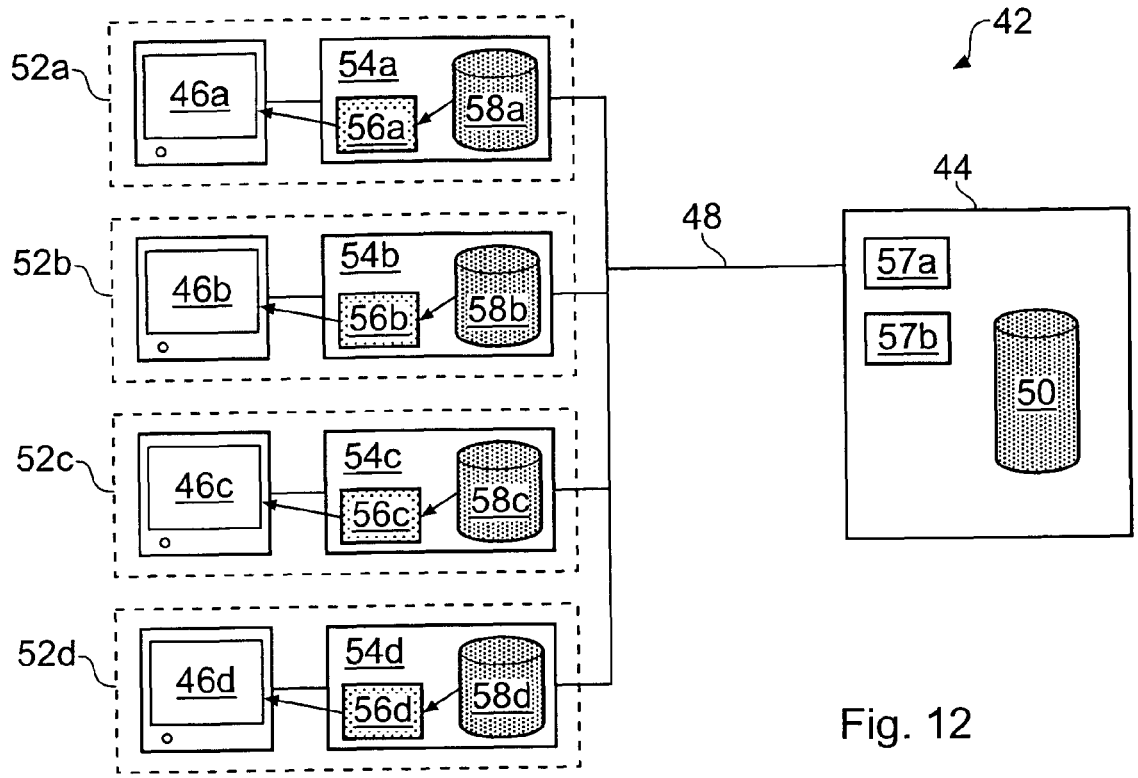

FIGS. 10, 11 and 12 show the workflows associated with performing the method shown in FIG. 6 in the context of the two server processors 57a, 57b servicing client workstations 52c-d. Except for the different client workstations being serviced by the server processors, and the fact that the other two client workstations are not idle but are operating autonomously, the workflows are similar to, and will be understood from, those shown in FIGS. 7, 8 and 9 respectively. It can be seen that throughout workflows shown in FIGS. 10, 11 and 12, the users of the original workstations remain able to work and are unaffected by the additional users.

Figure 13:
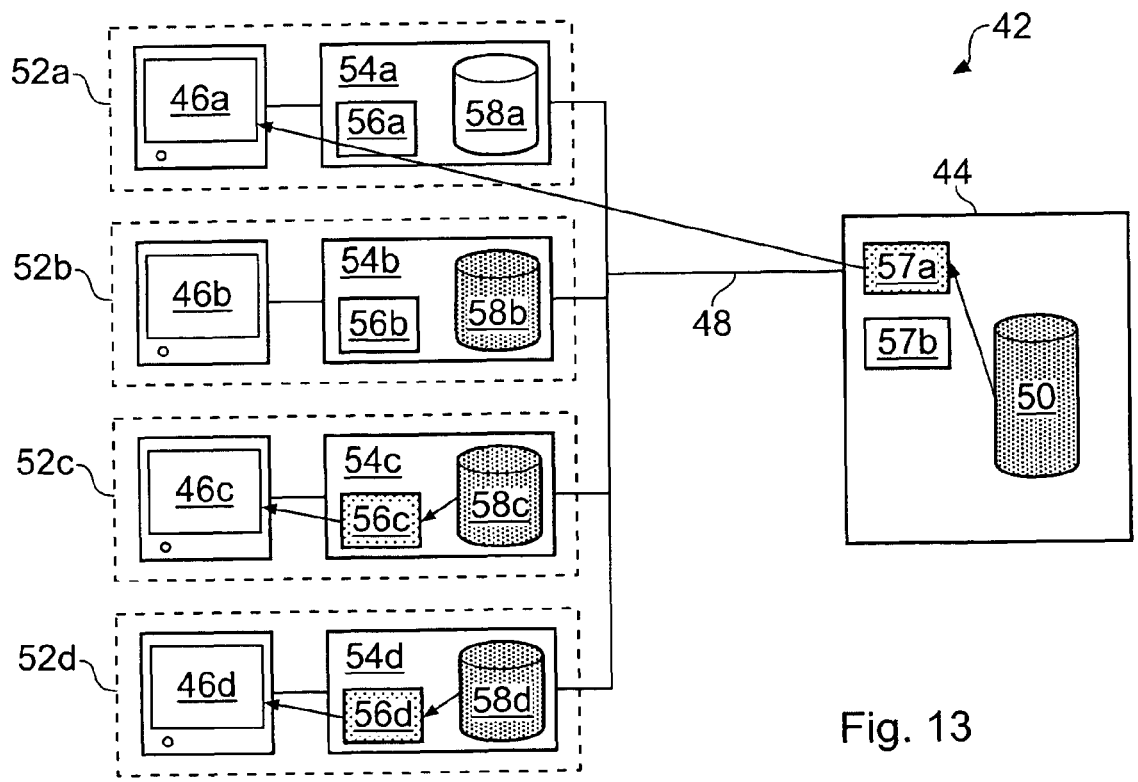

Thus, as shown in FIG. 12, all client workstations can end up working in a thick-client manner, but without having suffered a delay waiting for patient data to be transferred to their local memories. Furthermore, if a user of any of the client workstations wishes to study data not currently in their local memory, the network can return to a thin-client like architecture insofar as their workstation is concerned by returning to Step S2 of FIG. 6. This is schematically shown in FIG. 13 in which one of the client workstations (workstation 52a) is shown as having returned to being serviced by server processor 57a in a thin-client like manner. This allows the user to view images derived from the newly requested data without having to wait for it to be transferred to the client workstation. FIG. 13 also shows that the user of one of the client workstations (workstation 52b) has logged off, and so the client processor 56b associated with this workstation has become idle (shown not shaded). However, the most recently used patient data remains in the memory 58b of this workstation on the assumption that there is a reasonable chance it will still be needed when the workstation next becomes active (this way be optional depending on the data security policy). FIG. 13 shows the remaining workstations continuing to cycle between Steps S12 and S14 in a thick-client like manner.

Thus in a network having a server with sufficient processing capability only to service two client workstations at any one time in a thin-client like manner (i.e. without initial delay), all four are able to work without experiencing a delay associated with the initial transfer of patient data. Furthermore, the client workstations are able to operate autonomously, without loading the network, for much of the time.

In some situations it may be the case that a user sometimes works with data from a given patient only for a short period. This might be, for example, because he is briefly reviewing a large number of different data sets from different patients, and does not study any of them for any significant time. Thus it may be beneficial to delay transferring patient data from the server to the client for a period of time. This is because if it takes, for example, one-minute to transfer a patient's data, and the user is only analyzing each patient's data for 45 seconds, there is no benefit in transferring the data and doing so only increases network traffic unnecessarily. Thus if in a given implementation it is common for users to sometimes only analyze data sets for periods comparable to the time taken to transfer the data from the server to the client, there may be a requirement that transfer is delayed. For example, the delay might be twice the typical time that a user will analyze data if they are only briefly reviewing it, on the assumption that if they continue working with the data for at least this time, they are likely to remain working with the data long enough for it to he beneficial to transfer it to the client Alternatively, the server (or the client, depending on which is responsible for this aspect of the operation) may employ more advanced predictive techniques to determine whether to transmit patient data to the client. For example such techniques may relate to the user's recent activity pattern, the modality and acquisition parameters of the data, whether the data is a current or prior scan, and the user's personal profile. Such predictive techniques may be self-training based on the history of user activity.

The server will typically only support clients in a thin-client manner temporarily and so the infrastructure does not need to have the capacity to support all clients in this way at one time. Thus the capacity of the 3c server and the network interconnection only need to be scaled sufficiently to serve the estimated number of clients who have recently opened a study and have not yet had the relevant patient data transferred to their local memory. This number will in general be lower than the total number of active clients and will depend on:

the average time that users spend examining each study, and the average time it takes to transmit required patient data to a client workstation while it is being serviced as a thin client in the manner described above.

By way of example, if users spend an average of five minutes examining each patient's data, and it takes one minute to transmit the data to their workstation as a background operation, on average each client would function in a thin-client manner for 20% of the time (i.e. for the time that the patient data are being transferred to their memory), and would operate autonomously (i.e. in a thick-client like manner) for the remaining 80% of the time. Thus, in principle, one could equip the server with only ⅕th the number of processing units that would be required for a server serving only thin clients.

Since this estimate is based on a statistical average, in a practical implementation it may be beneficial have an excess margin of server processing power over the expected average requirement to accommodate variations in usage patterns. A small network (one with a small number of clients) will be more susceptible to statistical fluctuations in usage patterns than a large system (many clients). Thus, in practice the ratio of server processing power to clients to be serviced would vary, perhaps from something approaching 1:1 for a small system, to something asymptotically approaching the ratio required "on average" for a large system (i.e. time required to transfer data:time spent on each study). Thus the approach according to embodiments of the invention becomes of increased practical and economic benefit in the deployment of large networks.

Figure 14:
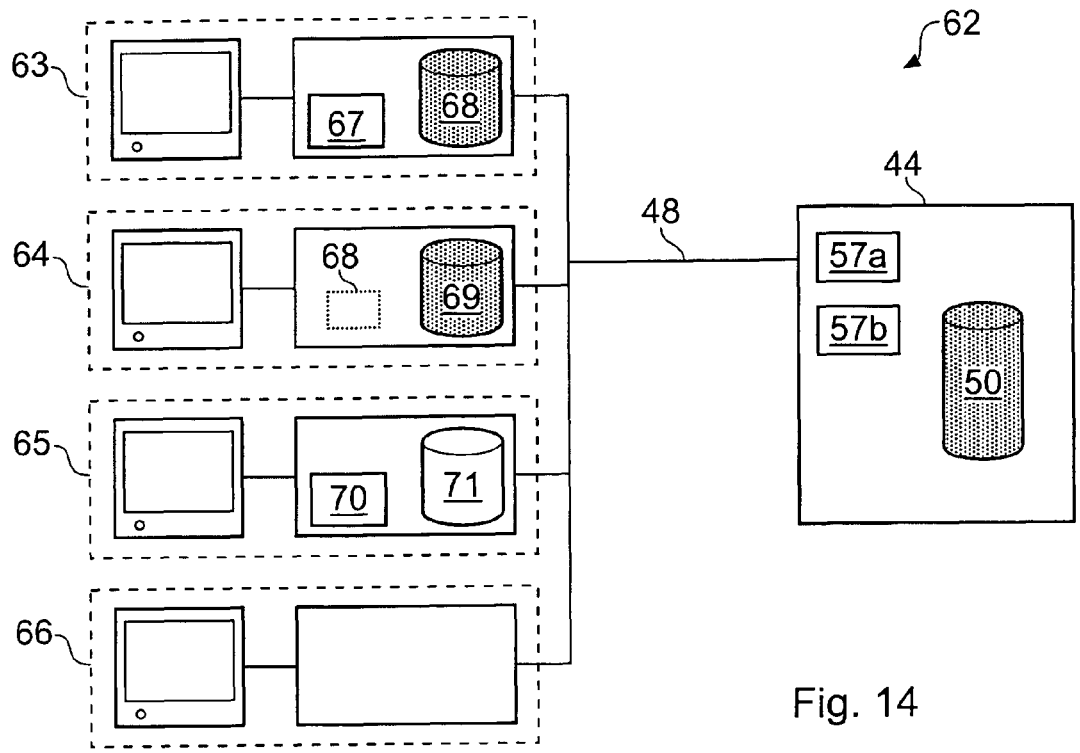
FIG. 14 schematically shows a computer network used in a hospital for processing and viewing medical image data according to another embodiment of the invention.

In addition to the above described benefits, embodiments of the invention offer further advantages when deployed in conjunction with techniques of adaptively selecting the location of processing (client processing or server processing) based on environmental factors such as availability of processing resources, data, and possibly network interconnection resources, FIG. 14 schematically shows a computer network 62 for analyzing (e.g. processing and viewing) medical image volume data according to another embodiment of the invention. The network 62 comprises a server 44 and a number (again four) of client computer workstations ("clients"). The server and clients are in data communication through a network interconnection 48. Elements of FIG. 13 which are similar to and will be understood from elements of FIG. 5 (primarily aspect of the server and network interconnection) are given the same reference numeral and not described further in the interest of brevity.

However, unlike the network 42 shown in FIG. 5, the client workstations of the network 62 shown in FIG. 13 are not identical. A first client workstation 63 includes both sufficient processing capability in its client processor 67, and sufficient data in its memory 68 (indicated by it being shaded) to execute the software application(s) supported by the network 62. This might be, for example, because it is a prestigious specialist's PC, or a high-end PC associated with (or a proprietary computer incorporated within) a CT scanner or other imaging modality. A second client workstation 64 includes sufficient data in its memory 69 to execute the software application(s) supported by the network 62 (again indicated by it being shaded), but insufficient processing capability for its client processor 68, to execute certain applications (indicated in FIG. 14 by a smaller box having a dashed outline). A third client workstation 65 has sufficient processing resources in its client processor 70 to execute the software application(s) supported by the network 62 and although having sufficient local memory 71, lacks the data to execute the application (for example because it is a public workstation). A fourth client workstation 66 has neither sufficient processing resource nor the required memory to execute the applications supported by the network, for example because it is a low-specification laptop computer.

Figure 15:
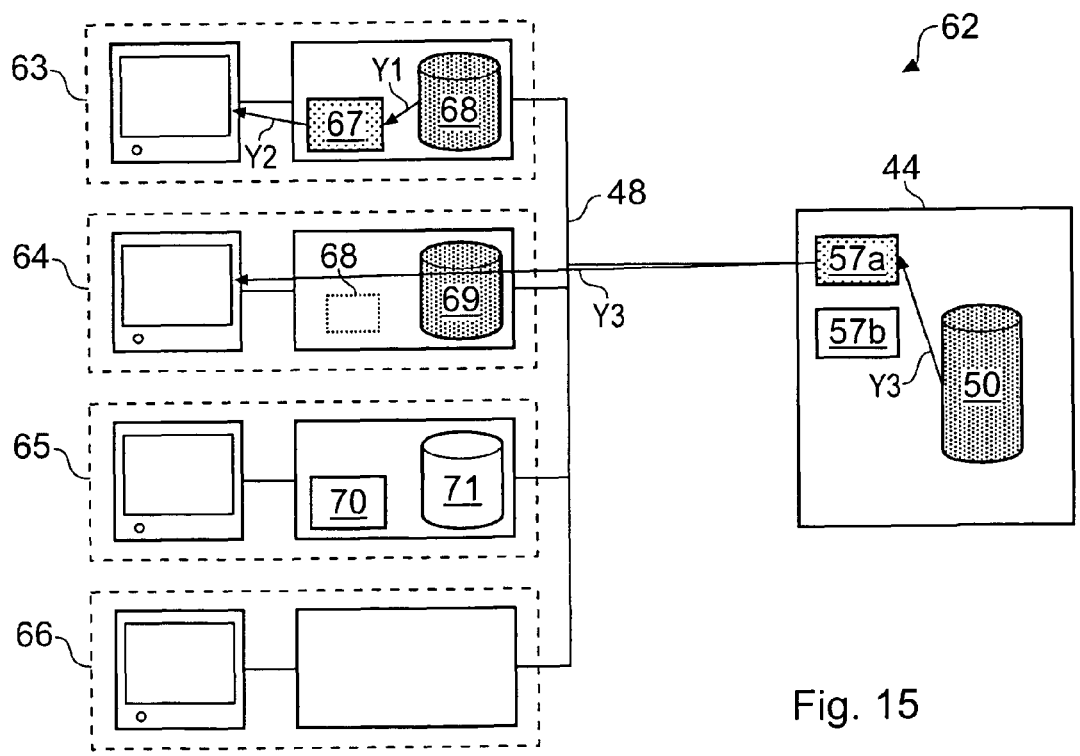
FIGS. 15 to 17 schematically show examples of workflow associated with the computer network of FIG. 14.
Figure 16:
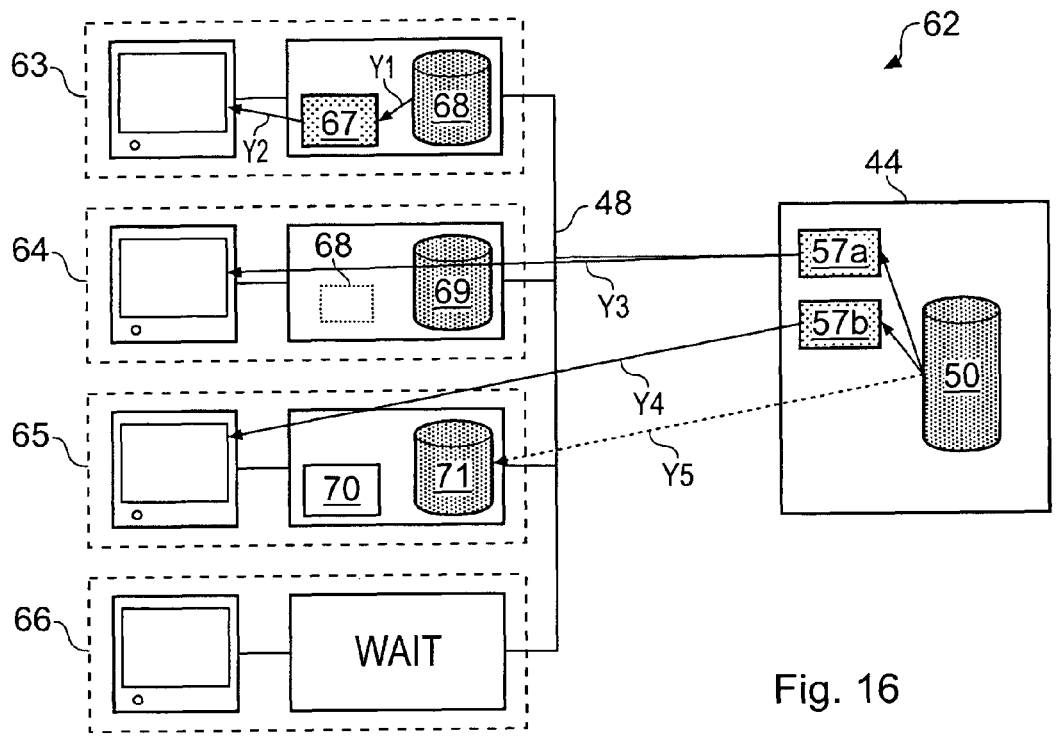
Figure 17:
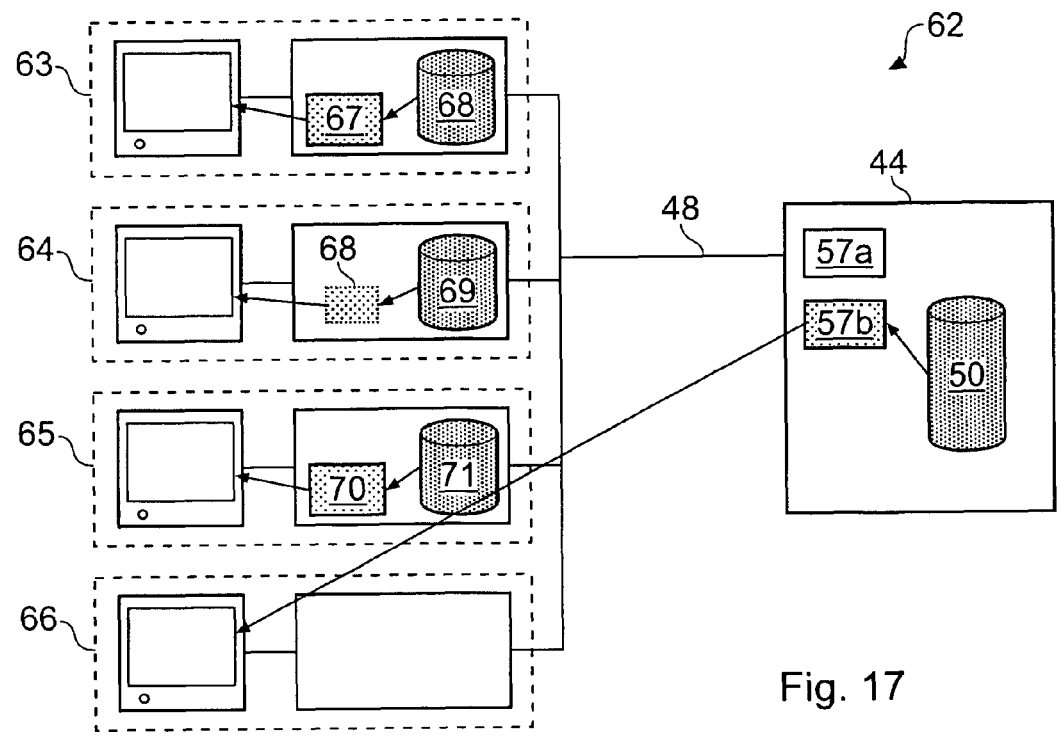

FIGS. 15 to 17 schematically show an example workflow for the network 62 shown in FIG. 14.

For the purpose of illustration, it is supposed that users first start working at the first 63 and second 64 client workstations. The first client workstation 63 works autonomously immediately since it has the data and the processing power it requires. This is schematically shown in FIG. 15 by arrows labeled Y1 and Y2. The second client workstation 64, on the other hand, operates in a thin-client like mode, i.e. it simply acts as a display for results generated by one of the server processor (in this case server processor 57a). This is schematically shown in FIG. 15 by the arrow labeled Y3. This is the only way the second client workstation's processor 68 can operate because it does not have sufficient resources for executing the software application required by its user.

Next, suppose users attempt to log on to the third 65 and fourth 66 client workstations. If the user of the third client workstation 65 starts ahead of the user of the fourth client workstation 66, the server loads the patient data required by the user of the third client workstation to one of its own processors (in this case server processor 57b because server processor 57a is already busy servicing the second client workstation), and starts to serve the third client workstation in a thin-client like manner. As this is happening, the third client workstation begins to retrieve the patient data from the data store 50 for storage in its own memory as a background operation so that it may operate in a thick-client like manner as described above in connection with FIG. 6. These steps of the workflow are schematically shown in FIG. 16 by the arrows labeled Y4 and Y5.

At this time, the user of the fourth client workstation 66 has to wait briefly (as indicated by the word "WAIT" in FIG. 16). This is because this workstation requires servicing by the server 44 to operate (because it does not have the processing power or data required to operate autonomously), but the server processors 57a, 57b are already busy servicing the second and third client workstations.

However, the situation is rapidly resolved in one of two ways. In one way, the user of the second client workstation 64 stops demanding such heavy processing so that its own processor 68 becomes able to satisfy the user's processing requirements and begins to process the data itself. Alternatively, the third client workstation finishes receiving its required patient data from the server and starts working autonomously. Either way, one of the server processors is freed up and becomes able to service the fourth client workstation 66 in a thin-client mode (this being the only mode in which the fourth client workstation 66 can operate because of its low level of resources). The workflow associated with both the second 64 and third 65 client workstations starting to perform their own processing (respectively due to a reduction in the user's processing requirements and the transfer of the required data to local memory), and the thin-client servicing of the fourth client workstation 66 are shown in FIG. 17.

Thus it can be seen that the above described techniques are flexible and can result in satisfactory performance and resource economy in a variety of client-server deployments, including the case of a deployment that is heterogeneous and adaptive regarding the choice of autonomous or server-based processing.

It will be understood that when operating in each of the different modes (i.e. thin-client like mode when following Steps S1 to S7 of FIG. 6, and thick-client like mode when following Steps S12 and S14), embodiments of the invention may employ techniques to optimize performance in the these modes of operation.

For example, in the thin-client like mode, the client may use a remote display abstraction such as (but not limited to): X11, VNC, Windows Terminal Services or Citrix Metaframe. The remote display abstraction may also include image compression. The image compression may be lossless (i.e. where decompressed images are digitally identical to the original) or may be lossy (i.e. where decompressed images are not identical to the original). Furthermore the compression may be a 3D compression, in other words the compression may utilize coherency between images in a third dimension. Furthermore, different components of each image to be transmitted during thin-client mode may be compressed differently according to the nature of the component. For example, in most situations, using a single encoding/compression for a screen display is not the most efficient way to compress the data. This is because the display is often comprised of multiple areas such as a background, a taskbar, a text window, a video window, a window with a medical image, graphical overlays, and so on. Each of these will be most efficiently compressed using a different algorithm. Thus it can be beneficial if the system is configured to analyze the media stream (i.e. the display to be transferred) which needs to be encoded, and decompose the stream into different objects, which are then compressed according to the most efficient algorithm for that type of object. Decomposition of the stream can be done using, for example, neural networks, pattern recognition and/or histogram analysis. E.g. pattern recognition could be used to identify an area of the screen where a medical image is shown, such as a chest image. This area may then be characterized as object type "chest image" and compressed accordingly. This approach has the advantage that each object has its own requirements as to image quality, compression ratio, latency etc. that can be tolerated, and the compression of each type of object can be tailored accordingly. Thus an overall improved display can be achieved for a given allocation of network bandwidth. This technique may be aided, for example, by a user, or program logic encoded in the client or server applications, providing input as to what different parts of the display are, and how they can be acceptably compressed.

Where compression is used, it may be beneficial to transfer a highly compressed version of the data to the client first so that the client can more quickly start rendering of the (admittedly highly compressed) data itself. Once the client has received the compressed data and is operating in a thick-client like manner working with the highly compressed data, the uncompressed (or less compressed) data, may be transferred so that that the client can switch to processing the higher quality data when it has been received. Furthermore, with this approach, rendering of the uncompressed data on the server may continue while the compressed data are rendered at the client. Thus high quality (on the server) and low quality (on the client) images are rendered in parallel. A choice may then be made as to made as to whether to display high quality images transmitted over the network, or low quality images generated locally. E.g. high quality rendered images from the server may be used for static images, but the low quality images from the client used for quickly displaying a series of images as a "movie".

Furthermore, techniques to reduce latency when operating in the thin-client like mode can be employed. Latency occurs in thin-client architectures because of the time delay associated with user inputs being executed due to the need for the inputs and responses being transferred over the network. To reduce latency, the system may include predictive techniques for determining the results of likely future user inputs, and transferring the results to the client workstation so that they can be rapidly displayed if the user does indeed follow one of the predicted user input paths. The predictions and associated processing can be made when the server processor is idle, e.g. while a user is studying a static image or in the small time interval between physical user input at the client and the receipt of the associated input data at the server. The predictions might include, for example common inputs such as rotate image, zoom, pan, etc. (It may be important, however, to ensure following through the processing associated with the predictions does not result in a state change of the application.)

In thin-client mode, the network may also be configured to transmitted. The regions of interest faster than the entire image to be displayed can be transmitted, The system may further include transmitting a "rough" version of the image for ready viewing and progressively refine the transmission with subsequent data transfer.

In thin-client mode, the client workstations may be configured to run an application that includes some application logic, including logic for generating the user interface, but excluding heavy processing or direct access to the application data, and where processing services associated with the server (including access to application data) are accessed through a remote access Application Programming Interface (API). The API may be a kind of Remote Procedure Call (RPC) API including, but not limited to, Unix RPC, DCOM, NET, SOAP. Alternatively, the remote access API may be a custom API carried over a custom protocol. The API may include a means for transmitting images between the server and client.

Processing may include an adaptive choice as to whether processing should execute on the server or on the client. The adaptive choice may be based, at least in part, on the processing resources available on the server and the client, and/or on the kind of data being manipulated or the kind of operation being performed. The choice may also be based on available hardware such as the existence or not of graphics acceleration equipment on the server or the client and/or the bandwidth of the network, e.g. in the server, the client, between them, or in terms of average sustained and/or peak bandwidth available between the server and client. The adaptive choice may also be based on an estimation of the likely incidence of network failures or delays between the server and client. Furthermore, the choice may be driven by a desire to detach clients from the network and have them work autonomously.

The network interconnection may be a wired network such as Ethernet, or, at least in part, a wireless network such as 802.11 (WiFi). The network infrastructure may also be provided by the Internet and/or through a low-bandwidth network, such as DSL or cable. The system may employ optimization techniques to provide improved performance in low-bandwidth or unstable-bandwidth conditions. The optimization may include caching of image data and replaying such image data when (some aspect of) the application returns to a previously visited state. The optimization may also include running elements of the user interface on the client so that they remain responsive even though communication with the server might be delayed and/or providing a fallback mechanism to recover smoothly from loss of communication with the server. Such mechanism may include periodic synchronization and "checkpointing" of application state data (metadata) on the server, so that they may be restored on the same or a different client when network problems are resolved.

The network may also include means to prevent the background transmission of patient data from interfering with the responsiveness of the clients while they are being served as thin clients. E.g. the means may include using different priorities for different kinds of data transmissions and/or using Quality of Service (QoS) guarantees to ensure timely transmission of certain data.

In some embodiments one or more client workstations, once they have received sufficient patient data to allow a desired software application to run (and associated metadata if required), may act as a server to a further one or more client workstation. Furthermore, in some embodiments, patient data (and if required metadata) may be transmitted from a first server to a second server, and once the data is transferred, the second server may take over the processing from the first server. In these cases, application state data (metadata) can be periodically transferred from the second server to the first server so that the first server can monitor the progress of the second server. The approach can be extended to allow arbitrary migration of the patient data, metadata, and processing function between any number of servers. The motivation for this may be to achieve load balancing, to make use of a server having more suitable (e.g. greater or faster) computing resources, to optimize the use of network bandwidth and/or achieving a higher bandwidth and/or lower latency connection to the client, and/or to provide redundancy and/or fault tolerance.

REFERENCES

[1] U.S. Pat. No. 6,384,821 (International Business Machines Corporation)
[2] U.S. Pat. No. 6,377,257 (International Business Machines Corporation)

What is claimed is:
1. A method of processing three-dimensional (3D) medical imaging volume data in a computer network comprising:
  a) providing a 3D volume data set to a server computer;
  b) initiating transfer of the 3D volume data set to a client computer over the network;
  c) performing rendering by processing the 3D volume data set at the server computer and transmitting the two-dimensional (2D) rendered images over the network to the client computer for display during the transfer of the 3D volume data set to the client computer; and
  d) switching to process the 3D volume data set at the client computer after the transfer of the 3D volume data set to the client computer is complete so as to continue further rendering at the client computer; and
  further comprising transmitting processing state data representing the operational state of the processing at the server computer from the server computer to the client computer before switching to process the 3D volume data set at the client computer, and configuring the client computer to a corresponding processing state using the processing state data before switching to process the 3D volume data set at the client computer.

2. A method according to claim 1, further comprising ceasing processing of the 3D volume data set at the server computer following transfer of the 3D volume data set to the client computer.

3. A method according to claim 1, further comprising transmitting processing state data representing the operational state of the processing at the client computer from the client computer to the server computer.

4. A method according to claim 1, wherein the 3D volume data set is transferred to the client computer from the server computer.

5. A method according to claim 1, wherein the 3D volume data set is transferred to the client computer from a data store.

6. A method according to claim 1, wherein the 3D volume data set is transferred to the client computer at times when there is no requirement for rendered images to be transmitted over the network.

7. A method according to claim 1, wherein the 3D volume data set is transferred to the client computer interspersed with the rendered images.

8. A method according to claim 1, further comprising digitally compressing the 3D volume data set before transfer to the client computer.

9. A method according to claim 8, further comprising transferring the 3D volume data set to the client computer following transfer of the compressed data set.

10. A method according to claim 1, further comprising digitally compressing the rendered images before transmitting them to the client computer.

11. A method according to claim 10, wherein a plurality of different compression methods are used to digitally compress the rendered images.

12. A method according to claim 1, further comprising waiting for a period of time before initiating transfer of the 3D volume data set to a client computer over the network.

13. A method according to claim 12, further comprising using predictive techniques to determine the period of time before initiating transfer of the 3D volume data set to a client computer over the network.

14. A method according to claim 13, wherein the predictive techniques used to determine the period of time before initiating transfer of the 3D volume data set take account of characteristics of the 3D volume data set.

15. A method according to claim 13, wherein the predictive techniques used to determine the period of time before initiating transfer of the 3D volume data set take account of previous user activity.

16. A method according to claim 13, wherein the predictive techniques used to determine the period of time before initiating transfer of the 3D volume data set are at least in part based on a self-training algorithm.

17. A method according to claim 1, further comprising displaying the rendered images to a user.

18. A computer network configured to perform the method of claim 1.

19. A computer program product comprising a non-tarnsitory machine readable medium bearing machine-executable instructions for implementing a rendering application for displaying two-dimensional (2-D) rendered images of three-dimensional (3D) volume data sets to a user, wherein the application is operable on a network interconnecting a server computer and a client computer to:

a) access a three-dimensional (3D) volume data set on the server computer;

b) initiate transfer of the 3D volume data set to a client computer over the network;

c) perform rendering by processing the 3D volume data set at the server computer and transmitting the two-dimensional (2D) rendered images over the network to the client computer for display during the transfer of the 3D volume data set to the client computer; and d) switch to process the 3D volume data set at the client computer after the transfer of the 3D volume data set to the client computer is complete so as to continue further rendering at the client computer; and further to transmit processing state data representing the operational state of the processing at the server computer from the server computer to the client computer before switching to process the 3D volume data set at the client computer and to configure the client computer to a corresponding processing state using the processing state data before switching to process the 3D volume data set at the client computer.

* * * * *